(12) United States Patent
Taranta et al.

(10) Patent No.: US 8,333,982 B2
(45) Date of Patent: Dec. 18, 2012

(54) AQUEOUS MICROEMULSIONS CONTAINING ORGANIC INSECTICIDE COMPOUNDS

(75) Inventors: Claude Taranta, Stutensee (DE); Wolfgang Meier, Limburgerhof (DE); Jens Raab, Deidesheim (DE); Matthias Bratz, Maxdorf (DE)

(73) Assignee: BASF SE, Ludwigshafen (DE)

( * ) Notice: Subject to any disclaimer, the term of this patent is extended or adjusted under 35 U.S.C. 154(b) by 150 days.

(21) Appl. No.: 12/671,744

(22) PCT Filed: Aug. 7, 2008

(86) PCT No.: PCT/EP2008/060380
§ 371 (c)(1),
(2), (4) Date: Feb. 2, 2010

(87) PCT Pub. No.: WO2009/019299
PCT Pub. Date: Feb. 12, 2009

(65) Prior Publication Data
US 2010/0234457 A1   Sep. 16, 2010

(30) Foreign Application Priority Data
Aug. 8, 2007 (EP) ................................. 07114027

(51) Int. Cl.
A01N 25/00 (2006.01)
A01N 37/34 (2006.01)
A61K 31/275 (2006.01)
A01P 7/04 (2006.01)

(52) U.S. Cl. ........................ 424/405; 514/520
(58) Field of Classification Search ............... 424/405; 514/520
See application file for complete search history.

(56) References Cited

U.S. PATENT DOCUMENTS

| | | | |
|---|---|---|---|
| 3,666,785 A | 5/1972 | Sakai et al. | |
| 4,272,920 A | 6/1981 | Dawson | |
| 4,283,222 A | 8/1981 | Horide et al. | |
| 4,541,860 A | 9/1985 | Civilla et al. | |
| 4,945,100 A | 7/1990 | Nyfeler et al. | |
| 4,973,352 A | 11/1990 | Heinrich et al. | |
| 5,045,311 A | 9/1991 | Pinter et al. | |
| 5,192,793 A | 3/1993 | Székely et al. | |
| 5,334,585 A | 8/1994 | Derian et al. | |
| 5,459,122 A * | 10/1995 | Ford et al. | 504/366 |
| 5,911,915 A | 6/1999 | Fonsny et al. | |
| 6,383,984 B1 * | 5/2002 | Aven | 504/116.1 |
| 6,455,471 B1 | 9/2002 | Gubelmann-Bonneau et al. | |
| 6,494,082 B1 | 12/2002 | Mizobe | |
| 6,602,823 B1 | 8/2003 | Röchling et al. | |
| 6,664,213 B1 | 12/2003 | Furusawa et al. | |
| 6,737,553 B1 | 5/2004 | Maas et al. | |
| 6,838,473 B2 * | 1/2005 | Asrar et al. | 514/365 |
| 7,256,317 B2 | 8/2007 | Maas et al. | |
| 2002/0098221 A1 * | 7/2002 | Taranta et al. | 424/405 |
| 2004/0157745 A1 | 8/2004 | Vermeer et al. | |
| 2007/0066489 A1 | 3/2007 | Vermeer et al. | |
| 2008/0153706 A1 | 6/2008 | Frisch et al. | |
| 2008/0214683 A1 | 9/2008 | Steinbrenner et al. | |
| 2010/0137375 A1 | 6/2010 | Finch | |
| 2010/0210461 A1 | 8/2010 | Stoesser et al. | |
| 2010/0227763 A1 | 9/2010 | Krapp et al. | |
| 2010/0234227 A1 | 9/2010 | Maier et al. | |
| 2010/0234457 A1 | 9/2010 | Taranta et al. | |
| 2011/0039698 A1 | 2/2011 | Taranta et al. | |
| 2011/0105333 A1 | 5/2011 | Israels et al. | |
| 2011/0124590 A1 | 5/2011 | Sowa et al. | |
| 2011/0195839 A1 | 8/2011 | Schlotterbeck et al. | |

FOREIGN PATENT DOCUMENTS

| | | |
|---|---|---|
| AU | 610388 | 11/1989 |
| CA | 2068826 | 11/1992 |
| CA | 1334274 | 2/1995 |
| DE | 69012487 | 2/1995 |
| DE | 19857963 | 6/2000 |
| EP | 0126430 | 11/1984 |
| EP | 0 160 182 | 11/1985 |
| EP | 0330904 | 9/1989 |
| EP | 0341126 | 11/1989 |
| EP | 0432062 | 6/1991 |
| EP | 0505053 | 9/1992 |
| EP | 0514769 | 11/1992 |
| EP | 0728414 | 8/1996 |
| EP | 1140741 | 10/2001 |
| EP | 1339281 | 6/2002 |
| EP | 1347681 | 6/2002 |

(Continued)

OTHER PUBLICATIONS

International Search Report in International Application No. PCT/EP2008/060380, filed Aug. 7, 2008.

(Continued)

Primary Examiner — Sreeni Padmanabhan
Assistant Examiner — Uma Ramachandran
(74) Attorney, Agent, or Firm — Brinks Hofer Gilson & Lione

(57) ABSTRACT

The present invention relates to new aqueous microemulsions containing one or more organic insecticide compounds and to their use for plant protection, including seed and crop protection, and protection of non-living material. The formulation according to the invention comprises:

a) at least one organic insecticide compound I having a water solubility of not more than 5 g/l at 298 K and 1013 mbar;

b) at least one polar organic solvent selected from ketones, esters, amides and ethers, each having from 6 to 8 carbon atoms;

c) at least one alcohol having from 6 to 8 carbon atoms;

d) at least one surfactant selected from anionic surfactants and non-ionic surfactants;

e) at least one non-polar organic solvent different from b); and f) water.

20 Claims, No Drawings

FOREIGN PATENT DOCUMENTS

| | | |
|---|---|---|
| EP | 1702607 | 9/2006 |
| EP | 1886560 | 2/2008 |
| FR | 2609631 | 7/1988 |
| RU | 2238649 | 10/2004 |
| WO | WO 90/06681 | 6/1990 |
| WO | WO 90/09103 | 8/1990 |
| WO | WO 93/15605 | 8/1993 |
| WO | WO 96/01305 | 1/1996 |
| WO | WO 99/66300 | 12/1999 |
| WO | WO 00/35278 | 6/2000 |
| WO | WO 00/78139 | 12/2000 |
| WO | WO 02/42488 | 5/2002 |
| WO | WO 02/43488 | 6/2002 |
| WO | WO 03/000053 | 1/2003 |
| WO | WO 03/022049 | 3/2003 |
| WO | WO 2005/105285 | 11/2005 |
| WO | WO 2006/030006 | 3/2006 |
| WO | WO 2006/114186 | 11/2006 |
| WO | WO 2007/017501 | 2/2007 |
| WO | WO 2007/028382 | 3/2007 |
| WO | WO 2007/028387 | 3/2007 |
| WO | WO 2007/028388 | 3/2007 |
| WO | WO 2007/057028 | 5/2007 |
| WO | WO 2007/110355 | 10/2007 |
| WO | WO 2008/043807 | 4/2008 |
| WO | WO 2008/061899 | 5/2008 |
| WO | WO 2009/019299 | 2/2009 |
| WO | WO 2009/133166 | 11/2009 |
| WO | WO 2010/010005 | 1/2010 |
| WO | WO 2010/040834 | 4/2010 |

OTHER PUBLICATIONS

Office Action dated May 30, 2012, from U.S. Appl. No. 13/122,790, filed Apr. 6, 2011.

Karakotov et al., "Tebuconazole-Based Fungicidal Composition," Shchelkovo Agrokhim Stock Chem., Jun. 19, 2003, XP002498611.

Mulqueen et al., "Recent Development in Suspoemulsions", Pestic. Sci., vol. 29, 1990, pp. 451-465.

Rhee et al., "Formulation of Parenteral Microemulsion Containing Itraconazole," Arch. Pharm. Res., vol. 30, No. 1, 2007, pp. 114-123.

Shell Chemicals, "Methyl PROXITOL Acetate," Mar. 16, 2007, XP007914204.

Skelton et al., "Formulation of Pesticide Microemulsions," Pesticide Formulations and Application Systems, vol. 8, 1988, pp. 36-45, XP002053622.

Tomšič et al., "Ternary Systems of Nonionic Surfactant Brij 35, Water and Various Simple Alcohols: Structural Investigations by Small-Angle X-ray Scattering and Dynamic Light Scattering," Journal of Colloid and Interface Science, vol. 294, 2006, pp. 194-211.

* cited by examiner

AQUEOUS MICROEMULSIONS CONTAINING ORGANIC INSECTICIDE COMPOUNDS

This application is a National Stage application of International Application No. PCT/EP2008/060380 filed Aug. 7, 2008, the entire contents of which is hereby incorporated herein by reference. This application also claims the benefit under 35 U.S.C. §119 of European Patent Application No.07114027.1, filed Aug. 8, 2007, the entire contents of which is hereby incorporated herein by reference.

The present invention relates to new aqueous microemulsions containing one or more organic insecticide compounds and to their use for plant protection, including seed and crop protection, and protection of non-living material.

BACKGROUND OF THE INVENTION

Organic insecticide compounds are often applied in the form of a dilute aqueous composition in order to achieve a good interaction with the target organisms. However, most active ingredients that are used as insecticides, in particular pyrethroid compounds, are only sparingly or even insoluble in water, i.e. they usually have a water-solubility of not more than 5 g/l, often not more than 1 g/l and particularly not more than 0.1 g/l at 25° C./1013 mbar. Therefore, formulators are often confronted with difficulties in formulating pesticide compounds in stable formulations that can be easily diluted with water.

Organic insecticides having a limited solubility in water are often formulated as aqueous suspension concentrate (SC) which can be diluted with water for use in the field. Suspension concentrates are formulations wherein the active ingredient is present in the form of finely divided solid particles, which are suspended in an aqueous dispersing medium utilizing surface-active compounds (surfactants), such as wetting agents, dispersants and rheological or suspending aids for stabilising the active ingredient particles in the dispersing medium. However, problems are often encountered with SC's as a result of settling during prolonged storage or storage at elevated temperatures, the resistance of settled particles to re-suspension and the formation of crystalline material upon storage. As a consequence, the formulations are difficult to handle and the bioefficacy may be inconsistent. Moreover, SC's are limited to actives that have a relatively high melting point. Most agrochemicals are sparingly water-soluble and become partly "deactivated" with water when formulated as an aqueous SC. Therefore, it is highly desirable to formulate these compounds as an oil in water microemulsion, hereinafter also referred to as ME or ME formulations.

Microemulsions are multiphase systems comprising a disperse phase and a continuous phase. In contrast to macro emulsions, the average particle (droplets) size (Z=average diameter as determined by light scattering) of the disperse phase in microemulsions is at least 5 times smaller than in macro emulsions and generally does not exceed 200 nm, while the average diameter of the droplets in macro emulsions is in μm range. Microemulsions are known as bicontinuous structures with intricate channels of oily and aqueous phases. Due to the small particle size (droplet size) of the disperse phase, or the intricate channels, microemulsions have a translucent appearance.

ME formulation of organic insecticide compounds are usually water based and additionally contain at least one surfactant and at least one cosolvent or cosurfactant, which is usually an organic solvent or a low molecular weight polyalkylene ether. By using ME formulations risks such as inflammability and toxicity, environmental concerns and costs are reduced in comparison with emulsifiable concentrate (EC) techniques, because water is the main constituent. Due to the small particle size of the disperse phase containing the active ingredient, an increase in bioavailability can often be achieved. However, it is difficult to maintain the stability of ME formulation of active ingredients having a low water-solubility with respect to the droplet size and uniformity and crystallization of active ingredient that may occur. Moreover, it is also difficult to maintain the droplet size stability when the ME formulation is diluted with water. However, a stable droplet size after dilution, i.e. maintaining a small droplet size, is important to achieve preferable biological activities. Therefore, much effort has been made in order to develop stable water-based microemulsion formulation. The aforementioned problems are particularly pronounced in case of pyrethroid compounds.

WO 90/06681 describes microemulsion formulations containing 0.01 to 1.0% of a solution containing one or more synthetic pyrethroid(s), $C_2$-$C_3$-alkoxylated nonylphenol, linear calcium dodecylbenzene sulfonate, polyoxyethylene sorbitan monolaurate and a mixture of organic solvents, and water ad 100%.

WO 99/66300 describes an aqueous microemulsion of an agriculturally active pyrethroid which comprises N-alkylated pyrrolidones, a EO/PO block copolymer surfactant, an ethoxylated castor oil or a tristyryl phenol ethoxylate, a phosphate ester as pH buffer and at least 80% of water.

EP 0160182 describes aqueous-based microemulsion compositions containing a synthetic pyrethroid, a surfactant blend, i.e. calcium dodecylbenzene sulfonate, ethoxylated distyrylphenol ammonium sulfate and ethoxylated tristyrylphenol, and adjuvants, such as antifoamers, antifreezing agents, thickeners and preservaties.

The microemulsions disclosed in prior art are solely suited for ULV application and not stable upon dilution with water. There is an ongoing need for ME formulations of organic insecticide compounds which are physically and chemically stable, i.e. upon storage no phase separation should be observed and the insecticide compound should not undergo remarkable degradation or suffer from inactivation. The ME formulations should have an intricate and stable structure. In particular, the formulation should be stable upon dilution with water, i.e. they should provide stable size distribution of small droplets after dilution with water. Moreover, they should provide reduced tendency of the active ingredient to crystallize, in particular after dilution of the formulation with water. Moreover the ME formulation should maintain its liquid monophasic state in a broad range of temperatures, i.e. in a range of from −10 to at least 50° C. In particular ME formulations are required which provide stable formulations of organic insecticides, in particular pyrethroid compounds, preferably pyrethroid esters having a biphenyl ether moiety and especially flucythrinate or alpha cypermethrin or mixtures thereof.

SUMMARY OF THE INVENTION

This object could surprisingly be achieved by providing a microemulsion formulation that contains at least one polar organic solvent selected from ketones, esters, amides and ethers, each having from 6 to 8 carbon atoms, at least one anti-freezing agent, selected from alcohols having from 6 to 8 carbon atoms, a surfactant mixture comprising at least one anionic surfactant and at least one non-ionic surfactant.

Therefore, the present invention relates to a formulation of organic insecticide compounds having a water solubility of not more than 5 g/l at 298 K and 1013 mbar in the form of an aqueous microemulsion, the formulation comprising a) at least one organic insecticide compound I having a water solubility of not more than 5 g/l at 298 K and 1013 mbar;
b) at least one polar organic solvent selected from ketones, esters, amides and ethers, each having from 6 to 8 carbon atoms;
c) at least one alcohol having from 6 to 8 carbon atoms;
d) at least one surfactant selected from anionic surfactants and non-ionic surfactants;
e) at least one non-polar organic solvent different from b); and
f) water.

The microemulsions of the present invention are stable liquid formulations that are clear and stable against formation of solids upon storage. Moreover they remain liquid at temperatures below −5° C., without losing their beneficial properties. Their freezing point is usually around −10° C.

The ME formulations of the invention can easily be diluted with water, e.g. prior to application with large amounts of water, e.g. from 5 to 10 000 parts of water per 1 part of the formulation, in particular from 10 to 5 000 parts of water per 1 part of the formulation, without the formation of coarse material and the aqueous dilutions have enhanced physical stability, i.e. the formation of solids after dilution is not observed even after storage for a prolonged period of time, e.g. after 24 h at room temperature no crystallization is observed. The quality of water used for dilution does not play a significant role; e.g. tap water as well as well water can be used.

Upon dilution with water, the compositions of the present invention form a bluish or even clear emulsion, indicating that the droplets/particles dispersed therein are of very small size. The average particle diameter of the droplets/particles will usually not exceed 200 nm, in particular 100 nm, more particularly 50 nm and may be 10 nm or even less than 10 nm. The small particle/size is maintained even after storage for a prolonged period of time, e.g. after storage for 24 h at room temperature the increase in particle size is generally less than 10%. The average particle size as referred herein, are Z-average particle diameters which can be determined by dynamic light scattering. A skilled person is familiar with these methods which are e.g. described in H. Wiese (D. Distler, Ed.), Aqueous Polymer Dispersions (Wässrige Polymerdispersionen), Wiley-VCH 1999, Chapter 4.2.1, p. 40ff, and the literature cited therein; H. Auweter, D. Horn, J. Colloid Interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429. Due to the small particle size after dilution with water the bioavailability and thus the biological activity of the active ingredient is often increased, in comparison with conventional formulations.

The microemulsions of the present invention will usually be an oil-in-water emulsion, i.e. water forms the continuous phase, while solvent and organic insecticide compound I is present in the disperse phase. They can be obtained for example by simply mixing the ingredients, by mixing a preformed solution of the organic insecticide compound I in the at least one polar organic solvent or in the at least one non-polar organic solvent either by adding water to the solution or by adding the solution to water.

In particular, ME formulations according to the present invention provide stable formulations of organic insecticide compounds, preferably pyrethroid compounds, in particular pyrethroid esters, more preferably pyrethroid esters having a biphenyl ether moiety and especially flucythrinate or alpha-cypermethrin or mixtures thereof.

DETAILED DESCRIPTION OF THE INVENTION

The term "alkyl" as used herein refers to saturated straight-chain or branched hydrocarbon radicals having the numbers of carbon atoms given in the prefix. Thus, $C_1$-$C_6$-alkyl refers to saturated straight-chain or branched hydrocarbon radicals having 1 to 4, 5 or 6 carbon atoms, especially 1 to 4 carbon atoms ($C_1$-$C_4$-alkyl) such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term "$C_2$-$C_6$-alkylene" as used herein refers to a saturated, divalent straight chain or branched hydrocarbon chains of 2, 3, 4, 5 or 6 carbon groups, examples including ethane-1,2-diyl, propane-1,3-diyl, propane-1,2-diyl, 2-methylpropane-1,2-diyl, 2,2-dimethylpropane-1,3-diyl, butane-1,4-diyl, butane-1,3-diyl (=1-methylpropane-1,3-diyl), butane-1,2-diyl, butane-2,3-diyl, 2-methyl-butan-1,3-diyl, 3-methyl-butan-1,3-diyl (=1,1-dimethylpropane-1,3-diyl), pentane-1,4-diyl, pentane-1,5-diyl, pentane-2,5-diyl, 2-methylpentane-2,5-diyl (=1,1-dimethylbutane-1,3-diyl) and hexane-1,6-diyl.

The term "aryl" as used herein refers to phenyl or naphthyl.

The microemulsion formulations of the present invention contain at least one polar organic solvent (b) selected from ketones, esters, amides and ethers having from 6 to 8 carbon atoms.

The term "ketone containing 6 to 8 carbon atoms" according to the present invention comprises aliphatic, cycloaliphatic and araliphatic ketones containing 6 to 8 carbon atoms. Examples of aliphatic ketones are 2-hexanone, 3-hexanone, 2-heptanone, 3-heptanone, 4-heptanone, 2-octanone, 3-octanone, 4-octanone and the like; examples of cycloaliphatic ketones are cyclohexanone, cycloheptanone and cyclooctanone, and one example of araliphatic ketones is acetophenone.

The term "ester containing 6 to 8 carbon atoms" according to the present invention comprises open chained aliphatic, cycloaliphatic and araliphatic esters as well as cyclic esters, also referred to as lactones, containing 6 to 8 carbon atoms. Examples for open chained esters are butyl acetate, tert.-butyl acetate, propylene glycol methyl ether acetate, pentyl acetate, hexyl acetate, propyl propionate, isopropyl propionate, butyl propionate, tert.-butyl propionate, pentyl propionate, propyl isopropionate, isopropyl isopropionate, butyl isopropionate, tert.-butyl isopropionate, pentyl isopropionate, propyl lactate, isopropyl lactate, butyl lactate, tert.-butyl lactate, pentyl lactate, ethyl butyrate, propyl butyrate, isopropyl butyrate, butyl butyrate, tert.-butyl butyrate, ethyl tert.-butyrate, propyl tert.-butyrate, isopropyl tert.-butyrate, butyl tert.-butyrate, tert.-butyl tert.-butyrate, methyl pentanoat, ethyl pentanoat, propyl pentanoat, isopropyl pentanoat, methyl hexanoat, ethyl hexanoat and methyl heptanoat. One example for araliphatic esters is methylbenzoate. Examples for lactones are hexanoic-gamma-lactone, heptanoic-gamma-lactone, octanoic-gamma-lactone, hexanoic-delta-lactone, heptanoic-delta-lactone or octanoic-delta-lactone.

The term "amide containing 6 to 8 carbon atoms" according to the present invention comprises open chained aliphatic, cycloaliphatic and araliphatic amides as well as cyclic amides, also referred to as lactams, containing 6 to 8 carbon atoms. Examples for open chained amides are N,N-dimethyl butyric acid amide, N,N-dimethyl pentanoic acid amide, N,N-dimethyl hexanoic acid amide, N,N-diethyl acetamide, N,N-diethyl propionic acid amide or N,N-diethyl butyric acid amide. Examples for lactams are N-ethyl gamma-lactam, N-propyl gamma-lactam, N-isopropyl gamma-lactam, N-butyl gamma-lactam, N-tert.-butyl gamma-lactam, N-methyl pentanoic gamma-lactam, N-ethyl pentanoic gamma-lactam, N-propyl pentanoic gamma-lactam, N-isopropyl pentanoic gamma-lactam, N-methyl hexanoic gamma-lactam, N-ethyl hexanoic gamma-lactam, N-methyl heptanoic-gamma-lactam, N-methyl delta-lactam (1-methyl-2-piperidinone), N-ethyl delta-lactam, N-propyl delta-lactam, N-isopropyl delta-lactam, N-methyl hexanoic-delta-lactam, N-ethyl hexanoic-delta-lactam or N-methyl heptanoic-delta-lactam.

The term "ether containing 6 to 8 carbon atoms" according to the present invention comprises aliphatic and cycloaliphatic ethers as well as cyclic ethers containing 6 to 8 carbon atoms. Examples are butyl ethyl ether, tert.-butyl ethyl ether, butyl propyl ether, tert.-butyl propyl ether, butyl isopropyl ether, tert.-butyl isopropyl ether, dibutylether, di-tert.-butylether, cyclohexyl methyl ether, cyclohexyl ethyl ether, phenol methyl ether (anisol), phenol ethyl ether, 2,2-dimethyltetrahydrofurane or 2,6-dimethyltetrahydrofurane.

In one preferred embodiment the at least one polar organic solvent is selected from ketones, lactones and lactams, each containing 6 to 8 carbon atoms.

More preferred are microemulsion formulations wherein the at least one polar organic solvent (b) is selected from the group consisting of aliphatic, cycloaliphatic and araliphatic ketones, such as 2-hexanone, 3-hexanone, cyclohexanone, 2-heptanone, 3-heptanone, 4-heptanone and acetophenone, lactames, such as 1-methyl-2-piperidinone, aliphatic, cycloaliphatic and araliphatic esters, such as propylene glycol methyl ether acetate and n-propyl(S)-lactate and aromatic ethers, such as anisol. Even more preferably the at least one polar organic solvent is selected from aliphatic, cycloaliphatic and araliphatic ketones having from 6 to 8 carbon atoms, in particular 2-hexanone, 3-hexanone, cyclohexanone, 2-heptanone, 3-heptanone, 4-heptanone and acetophenone, aliphatic, cycloaliphatic and araliphatic esters, such as propylene glycol methyl ether acetate and n-propyl lactate, and aromatic ethers, such as anisol.

Especially preferred are microemulsion formulations wherein the at least one polar organic solvent (b) is selected from 2-heptanone and acetophenone The amount of the polar organic solvent(s) in the microemulsion formulation according to the invention generally depends on the amount of organic insecticide compound I. In general, the weight ratio of the polar organic solvent(s) to the organic insecticide compound I is from 0.1:1 to 100:1, preferably from 0.5:1 to 50:1, in particular from 1:1 to 10:1. The total amount of polar organic solvent(s) will be generally in the range of 0.1 to 40% by weight, preferably 1 to 30% by weight, in particular from 2 to 25% by weight and more preferably from 5 to 20% by weight, based on the total weight of the formulation.

The microemulsion formulations of the present invention contain at least one alcohol (c) having from 6 to 8 carbon atoms. It is assumed that the alcohol serves as an anti-freezing agent.

The term "alcohol having from 6 to 8 carbon atoms" according to the present invention comprises hydrocarbons, preferably aliphatic or aromatic-aliphatic hydrocarbons having 6 to 8 carbon atoms and carrying at least one hydroxyl group, e.g. 1, 2, 3 or 4 OH groups, bound to an aliphatic carbon atom. Preferably the alcohols have 1 or 2 hydroxyl groups. Examples are 1-hexanol, 2-hexanol, 3-hexanol, 1-heptanol, 2-heptanol, 3-heptanol, 4-heptanol, 2-methylhexanol, 3-methylhexanol, 1-octanol, 1-octanol, 2-octanol, 3-octanol, 4-octanol, 2-ethylhexanol, 3-ethylhexanol, 1,6-hexanediol, 2,5-hexanediol, 1,7-heptanediol, 2,6-heptandiol, 1,8-octanediol, 2,7-octanediol, cyclohexanol, 1,2-cyclohexanediol, 1,4-cyclohexanediol, cycloheptanol, cyclooctanol and benzyl alcohol.

Preferably the at least one alcohol (c) is selected from 1-hexanol, 2-hexanol, 3-hexanol, 1-heptanol, 2-heptanol, 3-heptanol, 4-heptanol, 1-octanol, 2-octanol, 3-octanol, 4-octanol, 2-ethylhexanol, hexylene glycol, 2,5-hexanediol, cyclohexanol and benzyl alcohol. In particular the anti-freezing agent is hexylene glycol (1,6-hexanediol).

The amount of the at least one alcohol (c) in the microemulsion formulation according to the invention generally depends on the amount of organic insecticide compound I. In general, the weight ratio of alcohol (c) to the organic insecticide compound I is from 0.5:1 to 100:1, preferably from 1:1 to 50:1, in particular from 2:1 to 10:1. The total amount of alcohol (c) will be generally in the range of 1 to 40% by weight, in particular from 5 to 30% by weight and more preferably from 10 to 25% by weight, based on the total weight of the formulation.

The microemulsion formulation of the present invention also contains at least one surfactant (d). The term "surfactant" denotes surface active compounds, which, below, are also termed as detergent or emulsifier. The at least one surfactant serves to reduce surface tension between the continuous and the disperse phase, thereby stabilizing the droplets of the disperse phase. The surfactant also assists in the solubilisation of the organic insecticide compound I. Suitable surfactants for microemulsion formulations are well known in the art, e.g. from McCutcheon's Detergents and Emulsifiers, Int. Ed., Ridgewood, N.Y. The surfactants may be polymeric surfactants or non-polymeric surfactants. Preferably, the major amount, preferably at least 90%, in particular the total amount of surfactant present in the microemulsion is selected from non-polymeric surfactants, also termed emulsifier. Non-polymeric surfactants (emulsifiers), in contrast to polymeric surfactants, will generally have a molecular weight of below 2000 Dalton (number average), in particular from 150 to 2000 Dalton, preferably from 200 to 1500 Dalton.

Anionic surfactants include in particular the sodium, potassium, calcium or ammonium salts of
  $C_6$-$C_{22}$-alkylsulfonates such as lauryl sulfonate, isotridecylsulfonate;
  $C_6$-$C_{22}$-alkylsulfates such as lauryl sulfate, isotridecylsulfate, cetylsulfate and stearylsulfate;
  arylsulfonates, in particular $C_1$-$C_{16}$-alkylbenzene sulfonates, such as cumylsulfonate, octylbenzene sulfonate, nonylbenzene sulfonate, and dodecylbenzene sulfonate, naphthylsulfonate, mono- and di-$C_1$-$C_{16}$-alkylnaphthyl sulfonates such as dibutylnaphthylsulfonate;
  mono- and di-$C_1$-$C_{16}$-alkyldiphenylether (di)sulfonates such as dodecyldiphenylether disulfonate; sulfates and sulfonates of fatty acids and fatty acid esters;
  polyoxy-$C_2$-$C_3$-alkylene $C_8$-$C_{22}$-alkyl ether sulfates, in particular sulfates of ethoxylated $C_8$-$C_{22}$ alkanols such as sulfates of ethoxylated lauryl alcohol;

polyoxy-$C_2$-$C_3$-alkylene $C_1$-$C_{16}$-alkylbenzene ether sulfates, in particular sulfates of ethoxylated $C_1$-$C_{16}$-alkylphenols;

di $C_4$-$C_{18}$ alkyl esters of sulfosuccinic acid (=$C_4$-$C_{18}$-dialkyl sulfosuccinates) such as dioctylsulfosuccinate;

condensates of naphthalinesulfonic acid, $C_1$-$C_{16}$-alkyl naphthalinesulfonic acid or phenolsulfonic acid with formaldehyde (=($C_1$-$C_{16}$-alkyl)naphthalene sulfonate-formaldehyde condensates and phenolsulfonate formaldehyde condensates);

polyoxy-$C_2$-$C_3$-alkylene mono-, di- or tristyryl phenyl ether sulfates, in particular polyethoxylates of mono-, di- or tristyrylphenol;

mono- and di-$C_8$-$C_{22}$-alkyl sulfates;

polyoxy-$C_2$-$C_3$-alkylene $C_8$-$C_{22}$-alkyl ether phosphates;

polyoxy-$C_2$-$C_3$-alkylene $C_1$-$C_{16}$-alkylbenzene ether phosphates;

polyoxy-$C_2$-$C_3$-alkylene mono-di- or tristyryl phenyl etherphosphates; polyoxyethylene polycarboxylates, in particular homo- and copolymers of monoethylenically unsaturated mono- or dicarboxylic acids having from 3 to 8 carbon atoms, the copolymers also having polyethylene oxide side chains;

salts of fatty acids such as stearates; and polyphosphates such as hexametaphosphates and triphosphates (=tripoly-phosphate).

Non-ionic surfactants include in particular homo- or copolymers of $C_2$-$C_3$-alkyleneoxides, in particular EO homopolymers, PO homopolymers or EO/PO copolymers polyoxy-$C_2$-$C_3$-alkylene $C_8$-$C_{22}$-alkyl ethers, in particular polyethoxylates and poly-ethoxylates-co-propoxylates of linear or branched $C_8$-$C_{22}$-alkanols, more preferably polyethoxylated fatty alcohols and polyethoxylated oxoalcohols, such as polyethoxylated lauryl alcohol, polyethoxylated isotridecanol, polyethoxylated cetyl alcohol, polyethoxylated stearyl alcohol, and esters thereof, such as acetates;

polyoxy-$C_2$-$C_3$-alkylene aryl ethers and polyoxy-$C_2$-$C_3$-alkylene $C_1$-$C_{16}$-alkylaryl ethers, such as polyoxy-$C_2$-$C_3$-alkylene $C_8$-$C_{22}$-alkylbenzene ethers, in particular polyethoxylates of $C_1$-$C_{16}$-alkylphenoles, such as polyethoxylates of nonylphenol, decylphenol, isodecylphenol, dodecylphenol or isotridecylphenol, polyoxy-$C_2$-$C_3$-alkylene mono-, di- or tristyryl phenyl ethers, in particular polyethoxylates of mono-, di- and tristyrylphenoles; and the formaldehyde condensates thereof and the esters thereof, e.g. the acetates;

$C_6$-$C_{22}$-alkylglucosides and $C_6$-$C_{22}$-alkyl polyglucosides; polyethoxylates of $C_6$-$C_{22}$-alkylglucosides and polyethoxylates of $C_6$-$C_{22}$-alkyl polyglucosides;

polyethoxylates of fatty amines;

polyethoxylates of fatty acids and polyethoxylates of hydroxyl fatty acids;

partial esters of polyols with $C_6$-$C_{22}$-alkanoic acids, in particular mono- and diesters of glycerine and mono-, di- and triesters of sorbitan, such as glycerine monostearate, sorbitanmonooleat, sorbitantristearat;

polyethoxylates of partial esters of polyols with $C_6$-$C_{22}$-alkanoic acids, in particular polyethoxylates of mono- and diesters of glycerine and polyethoxylates of mono-, di- and triesters of sorbitan, such as polyethoxylates of glycerine monostearate, polyethoxylates of sorbitanmonooleat, polyethoxylates of sorbitanmonostearat and polyethoxylates of sorbitantristearat;

polyethoxylates of vegetable oils or animal fats such as corn oil ethoxylate, castor oil ethoxylate, tallow oil ethoxylate;

acetylene glycols such as 2,4,7,9-tetramethyl-4,7-bis(hydroxy)-5-decyne;

polyoxyethylene-polyoxypropylene-blockcopolymers; and polyethoxylates of fatty amines, fatty amides or of fatty acid diethanolamides.

The term polyoxy-$C_2$-$C_3$-alkylene ether refers to polyether radicals derived from ethylene oxide or propylene oxide. The term polyethoxylate refers to a polyether radical derived from ethylene oxide. Likewise, the term polyoxyethylene-co-polyoxypropylene refers to a polyether radical derived from a mixture of ethylene oxide and propylene oxide. The number of repeating units in the polyether radicals will generally vary from 2 to 100, frequently from 4 to 100 and in particular from 5 to 50.

Preferably, the at least one surfactant d) comprises of at least 50% by weight, based on the total amount of surfactant present, of a surfactant mixture, comprising at least one non-ionic surfactant and at least one anionic surfactant. In particular, the surfactant mixture amounts to at least 80% by weight, in particular at least 90% by weight, based on the total amount of surfactant present in the formulation. More preferably the surfactant is exclusively selected from the mixture of the at least one anionic surfactant and the at least one non-ionic surfactant.

Preferred anionic surfactants are selected from the aforementioned:

$C_1$-$C_{16}$-alkyl benzene sulfonates;

$C_1$-$C_{16}$-alkyl naphthalene sulfonates;

naphthalene sulfonate-formaldehyde condensates and $C_1$-$C_{16}$-alkyl naphthalene sulfonate-formaldehyde condensates;

polyoxy-$C_2$-$C_3$-alkylene $C_8$-$C_{22}$-alkyl ether sulfates;

polyoxy-$C_2$-$C_3$-alkylene $C_8$-$C_{22}$-alkyl ether phosphates;

polyoxy-$C_2$-$C_3$-alkylene $C_1$-$C_{16}$-alkylbenzene ether sulfates;

polyoxy-$C_2$-$C_3$-alkylene $C_1$-$C_{16}$-alkylbenzene ether phosphates, $C_8$-$C_{22}$-alkyl sulfates, $C_4$-$C_{18}$-dialkyl sulfosuccinates, polyoxy-$C_2$-$C_3$-alkylene mono-di- or tristyryl phenyl ether sulfates, polyoxy-$C_2$-$C_3$-alkylene mono-di- or tristyryl phenyl etherphosphates, polyoxyethylene polycarboxylates and polyphosphates, and mixtures thereof.

Particularly preferred anionic surfactants include the salts, in particular the sodium, potassium, calcium and ammonium salts of polyoxy-$C_2$-$C_3$-alkylene mono-di- or tristyryl phenyl ether sulfates.

Preferred non-ionic surfactants are selected from the aforementioned:

homo- or copolymers of $C_2$-$C_3$-alkyleneoxides, polyoxy-$C_2$-$C_3$-alkylene $C_8$-$C_{22}$-alkyl ethers, polyoxy-$C_2$-$C_3$-alkylene $C_8$-$C_{22}$-alkylbenzene ethers, polyoxy-$C_2$-$C_3$-alkylene mono-, di- or tristyryl phenyl ethers, polyoxy-$C_2$-$C_3$-alkylene mono- or distyryl phenyl ether-formaldehyde condensates, acetylene glycols and the mixtures thereof.

Particularly preferred non-ionic surfactants include polyoxy-$C_2$-$C_3$-alkylene $C_8$-$C_{22}$-alkyl ethers, homo- or copolymers of $C_2$-$C_3$-alkylene oxides and polyoxy-$C_2$-$C_3$-alkylene mono-, di- or tristyryl phenyl ethers, and mixtures thereof.

In a preferred embodiment of the invention, the at least one surfactant present in the microemulsion is selected from a surfactant mixture comprising:

d.1) at least one, e.g. one or two, anionic surfactant, and
d.2 at least one, e.g. one, two or three, non-ionic surfactant.

The weight ratio of anionic and non-ionic surfactant in the surfactant mixture is preferably from 0.1:1 to 10:1 in particular from 2:1 to 1:5.

In a very preferred embodiment of the invention, the surfactant present in the microemulsion is selected from a mixture comprising d.1) at least one anionic surfactant,
d.2.a) at least one non-ionic surfactant having a hydrophilic-lipophilic-balance (HLB) of 12 or below, in particular from 4 to 12, especially 5 to 11 and
d.2.b) at least one non-ionic surfactant having a hydrophilic-lipophilic-balance (HLB) of above 12, in particular from 13 to 18, especially 14 to 17.

The term "hydrophilic-lipophilic balance (HLB)" as used herein refers to a measure of the degree to which the surfactant is hydrophilic or lipophilic. The HLB value can be used to predict the surfactant properties of a molecule. According to the Davies method (Davies, J. T., Proceedings of the International Congress of Surface Activity, 1957, 426-438) this value can be determined using the following formula:

$$HLB = 7 + m*H^h + n*H^l$$

wherein m is the number of hydrophilic groups in the molecule, $H^h$ is a value corresponding to the specific hydrophilic character of the hydrophilic groups, n is the number of lipophilic groups in the molecule and $H^l$ is a value corresponding to the specific hydrophilic character of the lipophilic groups.

The non-ionic surfactant (d.2.a) having a HLB of 12 or below can be selected from any of the aforementioned non-ionic surfactants which have a HLB of 12 or below, in particular from 4 to 12 or 5 to 11. Suitable surfactants d.2.a include in particular polyoxy-$C_2$-$C_3$-alkylene $C_8$-$C_{22}$-alkyl ethers, polyoxy-$C_2$-$C_3$-alkylene $C_8$-$C_{22}$-alkylbenzene ethers and polyoxy-$C_2$-$C_3$-alkylene mono-, di- or tristyryl phenyl ethers. Preferably the at least one non-ionic surfactant d.2.a is selected from polyoxy-$C_2$-$C_3$-alkylene $C_8$-$C_{22}$-alkyl ethers, especially from polyoxy-$C_2$-$C_3$-alkylene $C_8$-$C_{22}$-alkyl ethers having a HLB in the range of from 4 to 11. More preferably the non-ionic surfactant d.2.a is selected from polyethoxylates and poly-ethoxylates-co-propoxylates of linear or branched $C_8$-$C_{22}$-alkanols. Examples of such preferred surfactants are ethoxylated branched $C_{1-3}$-alcohols as commercially available under the name Lutensol® TO3, Lutensol® TO5, Lutensol® TO7 or TO8.

The non-ionic surfactant (d.2.b) having a HLB of above 12 can be selected from any of the aforementioned non-ionic surfactants which have a HLB of above 12, in particular from 13 to 18 or 14 to 17. Suitable surfactants d.2.b include in particular homo- or copolymers of $C_2$-$C_3$-alkylene oxides, polyoxy-$C_2$-$C_3$-alkylene $C_8$-$C_{22}$-alkyl ethers, polyoxy-$C_2$-$C_3$-alkylene $C_8$-$C_{22}$-alkylbenzene ethers and polyoxy-$C_2$-$C_3$-alkylene mono-, di- or tristyryl phenyl ethers. Preferably the at least one non-ionic surfactant d.2.b. is selected from homo- or co-polymers of $C_2$-$C_3$-alkylene oxides or polyoxy-$C_2$-$C_3$-alkylene mono-, di- or tristyryl phenyl ethers, especially from homo- or copolymers of $C_2$-$C_3$-alkylene oxides or polyoxy-$C_2$-$C_3$-alkylene mono-, di- or tristyryl phenyl ethers having a HLB in the range of from 13 to 18, in particular from 14 to 17. More preferably the non-ionic surfactant d.2.b is selected from propylene oxide ethylene oxide block co-polymers or polyoxyethylene tristyryl phenyl ether. Examples of such preferred surfactants are ethoxylated tristyrylphenol as commercially available under the name Soprophor®, in particular Soprophor® 25 or Soprophor® 40, or propylene oxide ethylene oxide block co-polymers as commercially available under the name Pluronic® PE, in particular Pluronic® PE 6200 or Pluronic® 6400.

The total amount of the surfactants contained in the microemulsion formulation according to the invention generally depends on the amounts of organic insecticide compound I and of solvents. The weight ratio of surfactants to the total amount of organic insecticide compound I will usually be in the range from 0.5:1 to 100:1, preferably from 1:1 to 50:1, in particular from 2:1 to 10:1. Usually, the surfactants will be present in an amount ranging from 1 to 40% by weight, preferably from 5 to 35% by weight, in particular 10 to 30% by weight, based on the total weight of the microemulsion.

The microemulsion formulations of the present invention also contain at least one non-polar solvent (e) different from b). A wide variety of non-polar solvents can be used, such as aliphatic, cycloaliphatic or aromatic hydrocarbon solvents, vegetable oils, alkyl esters of fatty acids having more than 8 carbon atoms or mixtures thereof. Generally the non-polar solvents (e) have a water solubility of not more than 5 g/l, preferably not more than 1 g/l, at 298 K and 1013 mbar. Preferably the non polar solvent is selected from aromatic hydrocarbons, in particular from aromatic hydrocarbon compounds having from 8 to 11 carbon atoms, and mixtures thereof. Preferred non-polar solvents have a distillation range of from 130° C. to 300° C. at atmospheric pressure. Such non-polar solvents generally have a solubility in water of less than 1% by weight, in particular less than 0.1% by weight, based on the amount of water. Examples of such preferred non polar solvents are commercially available under the trade names Solvesso®, in particular Solvesso® 100, Solvesso® 150, Solvesso® 200, Solvesso® 150ND or Solvesso® 200ND, Aromatic®, in particular Aromatic® 150 and Aromatic® 200, Hydrosol®, in particular Hydrosol® A 200 and Hydrosol® A 230/270, Caromax®, in particular Caromax® 20 or Caromax® 28, aromat K 150, aromat K 200, Shellsol®, in particular Shellsol® A 100 or Shellsol® A 150, or Fin FAS-TX, in particular Fin FAS-TX 150 or Fin FAS-TX 200. Particular preference is given to microemulsion formulations containing as the non-polar solvent (e) Solvesso®, especially Solvesso® 200ND.

The amount of the at least one non-polar organic solvent (e) in the microemulsion formulation according to the invention generally depends on the amount of organic insecticide compound I. In general, the weight ratio of the non-polar organic solvent(s) (e) to the organic insecticide compound I is from 0.5:1 to 100:1, preferably from 1:1 to 50:1, in particular from 1.5:1 to 10:1. The total amount of the non-polar solvent(s) (e) will be generally in the range of 1 to 50% by weight, in particular from 5 to 40% by weight and more preferably from 10 to 30% by weight, based on the total weight of the formulation.

The total amount of solvents (b) and (e) and surfactants (d) in the microemulsion formulation according to the invention generally depends on the amount of organic insecticide compound I. In general, the weight ratio of organic solvents plus surfactants to the organic insecticide compound P is from 200:1 to 1:1, preferably from 100:1 to 1.5:1, in particular from 30:1 to 2:1. The total amount of solvents plus surfactants will be generally in the range of 10 to 90% by weight, in particular from 20 to 80% by weight and more preferably from 40 to 60% by weight, based on the total weight of the formulation.

The microemulsions of the invention also comprise at least one organic insecticide compound I which is sparingly soluble or insoluble in water. Preferably the solubility is below 1 g/l, frequently below 0.5 g/l and in particular below 0.1 g/l at 25° C. and 1013 mbar. The insecticide compound I is usually a non-polymeric compound, i.e. a compound having a defined molecular structure. The molecular weight of the insecticide compound I will generally not exceed 1000 Dalton, in particular 500 Dalton and is frequently from 150 to 500 Dalton.

The insecticide compound I can be selected from each group of active ingredients which are used to protect plants/crops from attack or infestation by insects or similar harmful invertebrate organisms such as arachnids, i.e. the insecticide compound I can be selected from insecticides, including insect attractants, insect growth regulators and insect repellents. Suitable insecticide compounds I are described in "The Pesticide Manual", 13th Edition, British Crop Protection Council (2003) among other publications and in http://www.hclrss.demon.co.uk.

The amount of insecticide compound I is usually in the range from 0.0001 to 20% by weight, frequently in the range from 0.01 to 10% by weight, in particular from 0.1 to 8% by weight and more preferably from 0.5 to 5% by weight, based on the total weight of the micro emulsion.

Organic insecticide compounds I include, but are not limited to:

I.1) Pyrethroid compounds, such as acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-, yfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, resmethrin, RU 15525, silafluofen, tefluthrin, tetramethrin, tralomethrin, transfluthrin, ZXI 8901;

I.2) Organo(thio)phosphates, such as acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

I.3) Carbamates, such as aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

I.4) Juvenile hormone mimics, such as hydroprene, kinoprene, methoprene, fenoxycarb, pyriproxyfen;

I.5) Nicotinic receptor agonists/antagonists compounds, such as acetamiprid, bensultap, cartap hydrochloride, clothianidin, dinotefuran, imidacloprid, thiamethoxam, nitenpyram, nicotine, spinosad (allosteric agonist), thiacloprid, thiocyclam, thiosultap-sodium, and AKD1022.

I.6) GABA gated chloride channel antagonist compounds, such as chlordane, endosulfan, gamma-HCH (lindane); acetoprole, ethiprole, fipronil, pyrafluprole, pyriprole, vaniliprole, the phenylpyrazole compound of formula I'

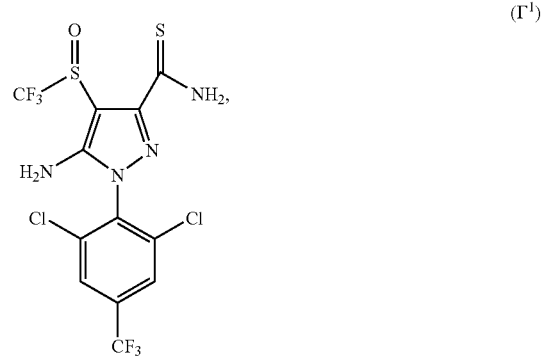

(I')

I.7) Chloride channel activators, such as abamectin, emamectin benzoate, milbemectin, lepimectin;

I.8) METI I compounds, such as fenazaquin, fenpyroximate, pyrimidifen, pyridaben, tebufenpyrad, tolfenpyrad, flufenerim, rotenone;

I.9) METI II and III compounds, such as acequinocyl, fluacyprim, hydramethylnon;

I.10) Uncouplers of oxidative phosphorylation, such as chlorfenapyr, DNOC;

I.11) Inhibitors of oxidative phosphorylation, such as azocyclotin, cyhexatin, diafenthiuron, fenbutatin oxide, propargite, tetradifon;

I.12) Moulting disruptors, such as cyromazine, chromafenozide, halofenozide, methoxyfenozide, tebufenozide;

I.13) Synergists, such as piperonyl butoxide, tribufos;

I.14) Sodium channel blocker compounds, such as indoxacarb, metaflumizone;

I.15) Fumigants, such as methyl bromide, chloropicrin sulfuryl fluoride;

I.16) Selective feeding blockers, such as crylotie, pymetrozine, flonicamid;

I.17) Mite growth inhibitors, such as clofentezine, hexythiazox, etoxazole;

I.18) Chitin synthesis inhibitors, such as buprofezin, bistrifluoron, chlorfluazuron, diflubenzuron, flucycloxuron, flufenoxuron, hexaflumuron, lufenuron, novaluron, noviflumuron, teflubenzuron, triflumuron;

I.19) Lipid biosynthesis inhibitors, such as spirodiclofen, spiromesifen, spirotetramat;

I.20) octapaminergic agonsits, such as amitraz;

I.21) ryanodine receptor modulators, such as flubendiamide;

I.22) Various, such as amidoflumet, benclothiaz, benzoximate, bifenazate, cyenopyrafen, cyflumetofen, chinomethionate, dicofol, pyridalyl, pyrifluquinazon;

I.23) N—R'-2,2-dihalo-1-R"cyclo-propanecarboxamide-2-(2,6-dichloro-α,α,α-tri-fluoro-p-toly)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl;

I.24) Anthranilamides, such as chloranthraniliprole, the compound of formula I'²

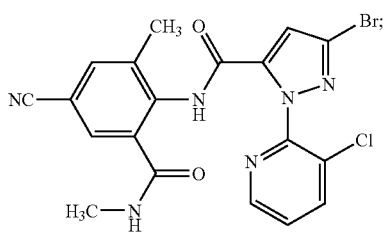

I.25) Malononitrile compounds, such as $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_3$, $CF_3CF_2CH_2C(CN)_2CH_2(CF_2)_3CF_2H$, 2-(2,2,3,3,4,4,5,5-octafluoropentyl)-2-(3,3,4,4,4-pentafluorobutyl)-malono-dinitrile, and $CF_2HCF_2CF_2CF_2CH_2C(CN)_2CH_2CH_2CF_2CF_3$, I.26) Alkynylether compounds I'⁴ and I'⁵:

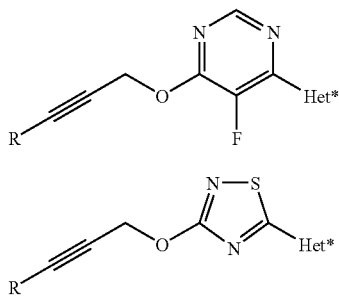

wherein R is methyl or ethyl and Het* is 3,3-dimethylpyrrolidin-1-yl, 3-methylpiperidin-1-yl, 3,5-dimethylpiperidin-1-yl, 3-trifluormethylpiperidin-1-yl, hexahydroazepin-1-yl, 2,6-dimethylhexahydroazepin-1-yl or 2,6-dimethylmorpholin-4-yl. These compounds are described e.g. in JP 2006131529.

The commercially available compounds of the group A may be found in The Pesticide Manual, 13th Edition, British Crop Protection Council (2003) among other publications.

Thioamides of formula I'¹ and their preparation have been described in WO 98/28279. Lepimectin is known from Agro Project, PJB Publications Ltd, November 2004. Benclothiaz and its preparation have been described in EP-A1454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chlorantraniliprole has been described in WO 01/70671, WO 03/015519 and WO 05/118552. Anthranilamide derivatives of formula I'² have been described in WO 01/70671, WO 04/067528 and WO 05/118552. Cyflumetofen and its preparation have been described in WO 04/080180. The aminoquinazolinone compound pyrifluquinazon has been described in EP A 109 7932. The malononitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, $CF_3CF_2CH_2C(CN)_2CH_2(CF_2)_3CF_2H$, 2-(2,2,3,3,4,4,5,5-octafluoropentyl)-2-(3,3,4,4,4-pentafluorobutyl)-malonodinitrile, and $CF_2HCF_2CF_2CF_2CH_2C(CN)_2CH_2CH_2CF_2CF_3$ have been described in WO 05/63694.

In a preferred embodiment the at least one insecticide compound I is selected from pyrethroid compounds, also referred to hereinafter as compounds P.

The term "pyrethroid compound P" includes natural and synthetic pyrethroids, including pyrethroid ether and pyrethroid esters, and synthetic pyrethroid analogs such as 1,4-diaryl-1-(cyclopropyl or isopropyl)-2-fluoro-2-butenes. Examples of pyrethroid compounds include pyrethroid esters such as acrinathrin, allethrin, barthrin, bifenthrin, bioallethrin, bioethanomethrin, biopermethrin, bioresmethrin, cis-methrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, esfenvalerate, fenfluthrin, fenpirithrin, fenpropathrin, fenvalerate, flucythrinate, fluvalinate, flurethrin, imiprothrin, metofluthrin, permethrin, phenothrin, prallethrin, profluthrin, pyresmethrin, pyrethrin I and II, resmethrin, tau-fluvalinate, tefluthrin, terallethrin, tetramethrin, tralomethrin and transfluthrin, pyrethroid ethers such as etofenprox, flufenprox, halfenprox, protrifenbute and silafluofen, and structurally comparable compounds such as 1-[1-(p-chlorophenyl)-2-fluoro-4-fluoro-3-phenoxphenyl)-2-butenyl]-cyclopropane (R,S)-(Z), and mixtures thereof.

Preferred pyrethroid compounds comprise a biphenyl ether moiety, wherein the phenyl ring may carry one or more, e.g. 1, 2 or 3 substituent radicals selected from fluorine or methyl. Preferred pyrethroid compounds according to the present invention are pyrethroid esters. These compounds can be described by the general formula P'

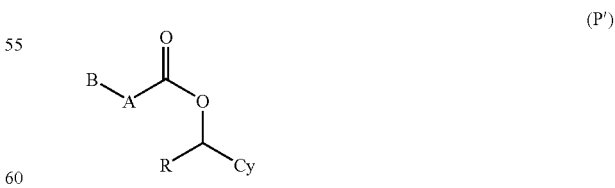

wherein
A is 2-methylpropan-1,1-diyl, cyclpropan-1,1-diyl, cyclopropan-1,2-diyl which may carry 1, 2 or 3 substituents selected from methyl and chlorine;
B is methyl, 1,2,2,2-tetrabromoethyl, phenyl, which may carry 1 or 2 radicals $R^b$, phenyl amino, which may carry 1 or 2 radicals $R^b$, wherein $R^b$ is selected from chlorine fluorine, trifluoromethyl, difluormethoxy, methoxy and ethoxy, or B is a radical $CR^x$=$CR^yR^z$, wherein $R^x$ is hydrogen or halogen, in particular chlorine or bromine, $R^y$, $R^z$ are independently of each other selected from fluorine, chlorine, bromine, methyl, $C_1$-$C_3$-alkoxyoxycarbonyl, such as methoxycarbonyl, ethoxycarbonyl or propoxycarbonyl and $C_1$-$C_3$-haloalkoxycarbonyl, such as difluoromethoxycarbonyl, trifluoromethoxycarbonyl, 2,2,2-trifluoroethoxycarbonyl, 1,1,1,3,3,3-hexafluoropropan-2-yl, or $R^y$, $R^z$ together are $C_3$-$C_5$-alkylene, e.g. 1,3-propandiyl, 1,4-butandiyl or 1,5-pentandiyl;

R is hydrogen or cyano and

Cy is a cyclic radical selected from phenyl and furyl, which are unsubstituted or which carry a radical selected from methyl, fluorine, methoxymethyl, phenyl, benzyl and phenoxy, and/or 1, 2, 3 or 4 radicals selected from methyl and fluorine and/or 2 radicals, which are bound of adjacent carbon atoms of phenyl form a moiety $OCH_2O$;

or Cy is imidazolidin-2,5-dion-1-yl, which may carry in the 3-position a radical selected from propen-3-yl and propyn-3-yl, hexahydroisoindol-1,3-dion-2-yl or $C_2$-$C_6$-alkenyl; or R and Cy together with the carbon atom to which they are bound form a 2,3-cyclopenten-1-on-4-yl radical, which may carry in the 4-position a radical selected from propen-3-yl, propyn-3-yl, 2-furylmethyl.

Preferably Cy is 4-phenoxyphenyl, wherein the phenyl ring may carry a radical selected from methyl, fluorine or chlorine. R is preferably cyano.

In a particular preferred embodiment the pyrethroid compound P is selected from alpha-cypermethrin and flucythrinate. Even more preferred the pyrethroid compound P is alpha-cypermethrin.

In particular, the pyrethroid compound P is the only organic insecticide compound in the microemulsion or amounts to at least 90% by weight of the total amount of organic insecticide compounds in the microemulsion.

The microemulsion of the invention also contains water. The amount of water is usually in the range from 1 to 80% by weight, frequently in the range from 5 to 50% by weight, in particular from 10 to 40% by weight and more preferably from 15 to 30% by weight, based on the total weight of the microemulsion. It is self-evident that the amount of water together with the amounts given for the other ingredients adds to 100% by weight.

In a preferred embodiment of the invention, the aqueous microemulsion formulation according to the present invention, comprises:

a) from 0.001 to 20% by weight of the at least one organic insecticide compound I;
b) from 0.1 to 40% by weight of the at least one polar organic solvent (c) mentioned herein;
c) from 1 to 30% by weight of the at least one alcohol having from 6 to 8 carbon atoms;
d) from 1 to 40% by weight of the at least one surfactant;
e) from 1 to 40% by weight of the at least one non-polar organic solvent; and
f) water ad 100% by weight.

The microemulsion formulation of the invention may contain further organic solvents different from (b), (c) and (e). If present, such further organic solvents are preferably selected from the group consisting of aromatic ethers, such as anisole, cyclic carbonates, such as propylene carbonate or butylene carbonate, lactones, such as gamma-butyro lactone, aromatic esters, such as $C_1$-$C_8$-alkyl benzoates, esters of dicarboxylic acids, such as di($C_1$-$C_4$-alkyl)glutarate, di($C_1$-$C_4$-alkyl)succinate or di($C_1$-$C_4$-alkyl)adipate, esters of alpha-hydroxy carboxylic acids, such as $C_1$-$C_8$-alkyl lactate, esters of phosphoric acid, such as tributyl phosphate, or dimethylsulfoxide (DMSO).

If present, such further organic solvents are frequently present in an amount of from 1 to 30% by weight, preferably from 2 to 20% by weight, based on the total weight of the formulation. Generally, however, the microemulsion formulation contains no or only a small amount of organic solvents different from the compounds (b), (c) and (e), i.e. the amount of solvent different from the compounds (b), (c) and (e) will generally not exceed 5% by weight and is preferably less than 2% or less than 1% by weight of the microemulsion formulation.

The microemulsion of the invention may further contain customary auxiliaries, such as defoamers, preservatives, colorants, stabilizers, stickers and the like which are usually employed in aqueous formulations of insecticides. The total amount of these auxiliaries will usually not exceed 15% by weight, in particular 10% by weight of the microemulsion. The total amount of these auxiliaries, except for anti-freezing agents will usually not exceed 5% by weight, in particular 3% by weight of the microemulsion.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. In general, the amount of preservatives will be from 0.1 to 10 g/l of the microemulsion composition.

Suitable defoamers include polysiloxanes, such as polydimethyl siloxane. Defoamers are usually employed in amounts of from 0.1 to 5 g/l of the microemulsion composition.

Suitable stabilizers comprise e.g. UV-absorbers such as cinnamic esters, 3,3 diphenyl 2-cyano acrylates, hydroxy and/or alkoxy substituted benzophenones, N (hydroxyphenyl)-benzotriazoles, hydroxyphenyl-s-triazines, oxalic amides and salicylates, e.g. the UVINUL® 3000, 3008, 3040, 3048, 3049, 3050, 3030, 3035, 3039, 3088, UVINUL® MC80 and radical scavengers, e.g. ascorbic acid, citric acid, sterically hindered amines (HALS-compounds) such as UVINUL® 4049H, 4050H and 5050H, and the like and antioxidants such as vitamin E. In a preferred embodiment the stabiliser is citric acid or ascorbic acid. In general, the amount of stabilizer will be from 0.01 to 10 g/l of the microemulsion composition.

Suitable stickers/adhesion agents include block copolymer EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers and copolymers derived from these polymers.

These customary auxiliaries may be contained within the composition of the present invention. However, it is also possible to add these auxiliaries after dilution with water to the ready-to-use aqueous composition.

The microemulsions of the present invention can be simply prepared by mixing the ingredients until an apparently homogeneous liquid has been formed. The sequence of the addition of the ingredients is of minor importance. For example the ingredients can be given into a vessel and the thus obtained mixture is homogenized, e.g. by stirring, until an apparently homogeneous liquid has been formed. However it is also possible to dissolve the organic insecticide compound I in at least one of the organic solvents (b) and or (e) or in the mixture of said solvent and surfactant and to mix the thus obtained solution with water and the remaining ingredients, e.g. by adding the solution to water or by addition of water to the solution. The temperature of mixing and the mixing conditions are of minor importance. Usually the ingredients are mixed at a temperature ranging from 10 to 90° C., in particular from 10 to 60° C. Higher temperatures, e.g. 35° C. or 40° C. or higher might be useful to expedite the formation of the microemulsion. However, mixing can also be achieved at lower temperatures e.g. from 10° C. to 35° C. or 40° C.

Depending on the type of organic insecticide compound I, the microemulsions of the invention are useful for combating a large number of harmful pests both in plant cultures and seeds but also in non-living material and in household.

The term "pests" or "harmful pests" as used herein relates to all types of pests which can be combated or controlled by organic insecticide compounds, including insect pest and arachnid pest.

Therefore the present invention also relates to
  the use of the microemulsions described herein for combating harmful pests; and
  a method of combating harmful organisms, which comprises contacting said harmful organisms, their habit, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of the microemulsions described herein.

In a first aspect of the invention the microemulsions described herein are used for plant protection, including treatment of seeds, in particular to the use for protecting crops from attack or infestation by harmful pests, i.e. for combating animal organisms that are harmful to plants or for protecting crops from attack or infestation by such a harmful organism. The present invention particularly relates to the use of the microemulsion for plant protection and in particular to a method of combating pests that are harmful to plants such as insects, arachnids or nematodes, in particular insects and arachnids, which method comprises contacting said harmful organisms, their habit, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of an aqueous microemulsions as described herein. The invention also relates to a method for protecting crops from attack or infestation by harmful pests, which comprises contacting a crop with an effective amount of an aqueous microemulsions as described herein.

In most instances, the microemulsions are diluted with water before being applied to the locus to be treated. The microemulsions of the invention are usually diluted with at least 1 part of water, preferably at least 10 parts of water, in particular at least 100 parts of water, e.g. with 1 to 10,000, in particular from 100 to 5,000 and more preferably with 500 to 2,000 parts of water per one part of the microemulsions (all parts are given in parts by weight).

Dilution will be usually achieved by pouring the microemulsions of the invention into water. Usually, dilution is achieved with agitation, e.g. with stirring, to ensure a rapid mixing of the concentrate in water. However, agitation is not necessary. Though the temperature of mixing is not critical, mixing is usually performed at temperatures ranging from 0 to 50° C., in particular from 10 to 30° C. or at ambient temperature.

The water used for mixing is usually tap water. However the water may already contain water soluble compounds which are used in plant protection, e.g. nutrients, fertilizers or water soluble pesticides.

The microemulsions of the invention after dilution are applied by usual means which are familiar to a skilled person.

The microemulsions of the present invention may e.g. be applied against the following pests:

Insect pests of the orders:
  Millipedes (Diplopoda) such as Blaniulus species
  Ants (Hymenoptera), such as Atta capiguara, Atta cephalotes, Atta laevigata, Atta robusta, Atta sexdens, Atta texana, Monomorium pharaonis, Solenopsis geminata, Solenopsis invicta, Pogonomyrmex species and Pheidole megacephala,
  Beetles (Coleoptera), such as Agrilus sinuatus, Agriotes lineatus, Agriotes obscurus and other Agriotes species, Amphimallus solstitialis, Anisandrus dispar, Anthonomus grandis, Anthonomus pomorum, Aracanthus morei, Atomaria linearis, Blapstinus species, Blastophagus piniperda, Blitophaga undata, Bothynoderes punciventris, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus and other Conoderus species, Conorhynchus mendicus, Crioceris asparagi, Cylindrocopturus adspersus, Diabrotica (longicornis) barberi, Diabrotica semi-punctata, Diabrotica speciosa, Diabrotica undecimpunctata, Diabrotica virgifera and other Diabrotica species, Eleodes species, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus and other Limonius species, Lissorhoptrus oryzophilus, Listronotus bonariensis, Melanotus communis and other Melanotus species, Meligethes aeneus, Melolontha hippocastani, Melolontha melolontha, Oulema oryzae, Ortiorrhynchus sulcatus, Oryzophagus oryzae, Otiorrhynchus ovatus, Oulema oryzae, Phaedon cochleariae, Phyllotreta chrysocephala, Phyllophaga cuyabana and other Phyllophaga species, Phyllopertha horticola, Phyllotreta nemorum, Phyllotreta striolata, and other Phyllotreta species, Popillia japonica, Promecops carinicollis, Premnotrypes voraz, Psylliodes species, Sitona lineatus, Sitophilus granaria, Sternechus pinguis, Sternechus subsignatus, and Tanymechus palliatus and other Tanymechus species,
  Flies (Diptera) such as Agromyza oryzae, Chrysomya bezziana, Chrysomya hominivorax, Chrysomya macellaria, Contarinia sorghicola, Cordylobia anthropophaga, Dacus cucurbitae, Dacus oleae, Dasineura brassicae, Delia antique, Delia coarctata, Delia platura, Delia radicum, Fannia canicularis, Gasterophilus intestinalis, Geomyza Tripunctata, Glossina morsitans, Haematobia irritans, Haplodiplosis equestris, Hypoderma lineata, Liriomyza sativae, Liriomyza trifolii, Lucilia caprina, Lucilia cuprina, Lucilia sericata, Lycoria pectoralis, Mayetiola destructor, Muscina stabulans, Oestrus ovis, Opomyza florum, Oscinella frit, Pegomya hysocyami, Phorbia antiqua, Phorbia brassicae, Phorbia coarctata, Progonya leyoscianii, Psila rosae, Rhagoletis cerasi, Rhagoletis pomonella, Tabanus bovinus, Tetanops myopaeformis, Tipula oleracea and Tipula paludosa, Heteropterans (Heteroptera), such as Acrosternum hilare, Blissus leucopterus, Cicadellidae such as Empoasca fabae, Chrysomelidae, Cyrtopeltis notatus, Delpahcidae, Dysdercus cingulatus, Dysdercus intermedius, Eurygaster integriceps, Euschistus impictiventris, Leptoglossus phyllopus, Lygus lineolaris, Lygus pratensis, Nephotettix species, Nezara viridula, Pentatomidae, Piesma quadrata, Solubea insularis and Thyanta perditor, Aphids and other homopterans (Homoptera), e.g. Acyrthosiphon onobrychis, Adelges laricis, Aphidula nasturtii, Aphis fabae, Aphis forbesi, Aphis glycines, Aphis gossypii, Aphis grossulariae, Aphis pomi, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes (Myzus) persicae, Myzus ascalonicus, Myzus cerasi, Myzus varians, Nasonovia ribis-nigri, Nilaparvata lugens, Pemphigus bursarius, Pemphigus populivenae, and other Pemphigus species, Perkinsiella saccharicida, Phorodon humuli, Psyllidae such as Psylla mali, Psylla piri and other Psylla species, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, and Viteus vitifolii;

Lepidopterans (Lepidoptera), for example Agrotis ypsilon, Agrotis segetum and other Agrotis species, Alabama argillacea, Anticarsia gemmatalis, Argyresthia conjugella, Autographa gamma, Bupalus piniarius, Cacoecia murinana, Capua reticulana, Chematobia brumata, Chilo suppresalis and other Chilo species, Choristoneura fumiferana, Choristoneura occidentalis, Cirphis unipuncta, Cnaphlocrocis medinalis, Cydia pomonella, Dendrolimus pini, Diaphania nitidalis, Diatraea grandiosella, Earias insulana, Elasmopalpus lignosellus, Eupoecilia ambiguella, Euxoa species, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Lerodea eufala, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Momphidae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sesamia nonagrioides and other Sesamia species, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis, Orthopterans (Orthoptera), such as Acrididae, Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

Termites (Isoptera), such as Calotermes flavicollis, Coptotermes species, Dalbulus maidis, Leucotermes flavipes, Macrotermes gilvus, Reticulitermes lucifugus and Termes natalensis;

Thrips (Thysanoptera) such as Frankliniella fusca, Frankliniella occidentalis, Frankliniella tritici and other Frankliniella species, Scirtothrips citri, Thrips oryzae, Thrips palmi, Thrips simplex and Thrips tabaci;

and

Arachnoidea, such as arachnids (Acarina), for example e.g. of the families Argasidae, Ixodidae and Sarcoptidae, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei, and Eriophyidae species such as Aculus schlechtendali, Phyllocoptrata oleivora and Eriophyes sheldoni; Tarsonemidae species such as Phytonemus pallidus and Polyphagotarsonemus latus; Tenuipalpidae species such as Brevipalpus phoenicis; Tetranychidae species such as Tetranychus cinnabarinus, Tetranychus kanzawai, Tetranychus pacificus, Tetranychus telarius and Tetranychus urticae, Panonychus ulmi, Panonychus citri, and Oligonychus pratensis.

If the microemulsion according to the invention contain a organic insecticide compound which is active against rice pathogens, the composition may also be used to combat rice phatogens such as rice water weevil (Lissorhoptrus oryzaphilus), rice stem borer (Chilo suppresalis), rice leaf roller, rice leaf beetle, rice leaf miner (Agromyca oryzae), leafhoppers (Nephotettix spp.; especially smaller brown leafhopper, green rice leafhopper), planthoppers (Delphacidae; especially white backed planthopper, brown rice planthopper), stinkbugs.

The microemulsions according to the invention can be applied in conventional manner, usually as an aqueous dilution which is obtained by diluting the microemulsions with water. The required application rate of the pure active compounds without formulation auxiliary depends on the density of the harmful infestation, on the development stage of the plants, on the climatic conditions of the location where the composition is used and on the application method. In general, the application rate is from 0.001 to 3 kg/ha, preferably from 0.005 to 2 kg/ha and in particular from 0.01 to 1 kg/ha, from 0.1 g/ha to 1 kg/ha, from 1 g/ha to 500 g/ha or from 5 g/ha to 500 g/ha of active substance.

The diluted microemulsions are applied to the plants mainly by spraying, in particular foliar spraying. Application can be carried out by customary spraying techniques using, for example, water as carrier and spray liquor rates of from about 100 to 1000 l/ha (for example from 300 to 400 l/ha).

Moreover, it may be useful to apply the microemulsions according to the invention jointly as a mixture with other crop protection products, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

In a further embodiment of the invention, the microemulsions contain an organic insecticide compound which is active against non-crop pests. Therefore the invention also relates to a method for controlling non-crop pests comprising contacting the pests or their food supply, habitat, breeding grounds or their locus with the microemulsion according to the invention.

The invention further relates to the use of a microemulsion according to the invention for the protection of non-living organic materials against non-crop pests.

Non-crop pests are pests of the classes Chilopoda and Diplopoda and of the orders Isoptera, Diptera, Blattaria (Blattodea), Dermaptera, Hemiptera, Hymenoptera, Orthoptera, Siphonaptera, Thysanura, Phthiraptera, Araneida, Parasitiformes and Acaridida, for example:

- centipedes (Chilopoda), e.g. Scutigera coleoptrata,
- millipedes (Diplopoda), e.g. Narceus spp.,
- spiders (Araneida), e.g. Latrodectus mactans, and Loxosceles reclusa,
- scabies (Acaridida): e.g. sarcoptes sp,
- ticks and parasitic mites (Parasitiformes): ticks (Ixodida), e.g. Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata and parasitic mites (Mesostigmata), e.g. Ornithonyssus bacoti and Dermanyssus gallinae,
- termites (Isoptera), e.g. Calotermes flavicollis, Leucotermes flavipes, Heterotermes aureus, Reticulitermes flavipes, Reticulitermes virginicus, Reticulitermes lucifugus, Termes natalensis, and Coptotermes formosanus,
- cockroaches (Blattaria-Blattodea), e.g. Blattella germanica, Blattella asahinae, Periplaneta americana, Periplaneta japonica, Periplaneta brunnea, Periplaneta fuligginosa, Periplaneta australasiae, and Blatta orientalis,
- flies, mosquitoes (Diptera), e.g. Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates spp., Hypoderma lineata, Leptoconops torrens, Lucilia caprina, Lucilia cuprina, Lucilia sericata, Lycoria pectoralis, Mansonia spp., Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola, and Tabanus similis,
- Earwigs (Dermaptera), e.g. forficula auricularia,
- true bugs (Hemiptera), e.g. Cimex lectularius, Cimex hemipterus, Reduvius senilis, Triatoma spp., Rhodnius prolixus, and Arilus critatus,
- ants, bees, wasps, sawflies (Hymenoptera), e.g. Crematogaster spp., Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Dasymutilla occidentalis, Bombus spp. Vespula squamosa, Paravespula vulgaris, Paravespula pennsylvanica, Paravespula germanica, Dolichovespula maculata, Vespa crabro, Polistes rubiginosa, Camponotus floridanus, and Linepithema humile,
- crickets, grasshoppers, locusts (Orthoptera), e.g. Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera, and Locustana pardalina,
- fleas (Siphonaptera), e.g. Ctenocephalides felis, Ctenocephalides canis, Xenopsylla cheopis, Pulex irritans, Tunga penetrans, and Nosopsyllus fasciatus,
- silverfish, firebrat (Thysanura), e.g. Lepisma saccharina and Thermobia domestica,
- lice (Phthiraptera), e.g. Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus and Solenopotes capillatus.

The present invention also relates to a method for the protection of non-living organic materials against non-crop pests as mentioned above comprising contacting the pests or their food supply, habitat, breeding grounds, their locus or the non-living organic materials themselves with a pesticidally effective amount of a formulation according to the invention.

Furthermore, a formulation according to the invention can be used for protecting cellulose-containing non-living organic materials, e.g. for protecting cellulose-containing non-living organic materials against non-crop pests from the Isoptera, Diptera, Blattaria (Blattodea), Hymenoptera, and Orthoptera orders, most preferably the Isoptera orders.

The present invention also provides a method for protecting cellulose-containing non-living organic materials against non-crop pests, preferably from the Isoptera, Diptera, Blattaria (Blattodea), Hymenoptera, and Orthoptera orders, most preferably the Isoptera orders, comprising contacting the pests or their food supply, habitat, breeding ground, their locus or the cellulose-containing non-living organic materials themselves with a formulation according to the invention comprising at least an insecticide.

Furthermore, a composition according to the invention comprising at least one organic insecticide can be used for protection of animals against non-crop pest of the class Chilopoda, and of the orders Araneida, Hemiptera, Diptera, Phthiraptera, Siphonaptera, Parasitiformes and Acaridida by treatment of the pests in water bodies and/or in and around buildings, including but not limited to walls, ground, manure piles, turf grass, pastures, sewers and materials used in the construction of buildings and also mosquito nets, mattresses and bedding, with a formulation according to the present invention.

Animals include warm-blooded animals, including humans and fish. Thus, a formulation according to the invention comprising at least an insecticide can be used for protection of warm-blooded animals such as cattle, sheep, swine, camels, deer, horses, poultry, rabbits, goats, dogs and cats.

Furthermore, a formulation according to the invention can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). A formulation according to the invention comprising at least an insecticide can be applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant control composition of the present invention is directly applied to the nest of the ants or to its surrounding or via bait contact.

Furthermore, a microemulsion according to the invention can be applied preventively to places at which occurrence of the pests is expected.

In a further aspect, the invention relates to the treatment of seeds. The term seed treatment comprises all suitable seed treatment techniques known in the art, such as, but not limited to, seed dressing, seed coating, seed soaking, seed film coating, seed multilayer coating, seed encrusting, seed dripping, and seed pelleting. The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

If the microemulsion according to the present invention is intended for seed treatment purposes, the formulation may optionally comprise also dyes or pigments. Suitable pigments or dyes for seed treatment formulations are pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The invention furthermore comprises seeds treated with the microemulsion according to the present invention.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugar beet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, microemulsion may also be used for the treatment of seeds from plants, which tolerate the action of herbicides or fungicides or insecticides or nematicides owing to breeding, mutation and/or genetic engineering methods.

For example, microemulsion can be employed in transgenic crops which are resistant to herbicides from the group consisting of the sulfonylureas (EP A 0 257 993, U.S. Pat. No. 5,013,659), imidazolinones (see for example U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), glufosinate-type (see for example EP-A-0 242 236, EP-A-242 246) or glyphosate-type (see for example WO 92/00377) or in plants resistant towards herbicides selected from the group of cyclohexadienone/aryloxyphenoxypropionic acid herbicides (U.S. Pat. Nos. 5,162,602, 5,290,696, 5,498,544, 5,428,001, 6,069,298, 6,268,550, 6,146,867, 6,222,099, 6,414,222) or in transgenic crop plants, for example cotton, with the capability of producing Bacillus thuringiensis toxins (Bt toxins) which make the plants resistant to certain pests (EP A 0 142 924, EPA 0 193 259).

Furthermore, microemulsion can be used also for the treatment of seeds from plants, which have modified characteristics in comparison with existing plants, and which can be generated for example by traditional breeding methods and/or the generation of mutants, or by recombinant procedures. For example, a number of cases have been described of recombinant modifications of crop plants for the purpose of modifying the starch synthesized in the plants (e.g. WO 92/11376, WO 92/14827, and WO 91/19806) or of transgenic crop plants having a modified fatty acid composition (WO 91/13972).

The seed treatment application is carried out by spraying or dusting the seeds with an effective amount of the microemulsion before sowing of the plants and before emergence of the plants.

In the treatment of seeds the corresponding microemulsions are applied by treating the seeds with an effective amount of the microemulsion. Herein, the application rates of the organic insecticide compound I are generally from 0.1 g to 10 kg per 100 kg of seed, preferably from 1 g to 5 kg per 100 kg of seed, in particular from 1 g to 2.5 kg per 100 kg of seed. For specific crops such as lettuce and onions the rates can be higher.

The following examples shall further illustrate the present invention. The scope of this invention should not be deemed limited by the examples, but encompasses the entire subject matter defined in the claims. In the examples, all percentage is percent by weight of the total composition.

I Analytics:

Particle sizes can be determined by dynamic light scattering, e.g. with a Zetasizer Nano ZS from Malvern Instruments, a Nanotrac from Particle Metrix GmbH or a Nanofox from Sympatec. Generally, particle sizes are determined on diluted formulations (in water) at 25° C.

II. Preparation of the Formulations of the Invention:

EXAMPLE 1

The entire ingredients as given in table 1 were added into a vessel equipped with a stirrer and the mixture was stirred at 55° C. for 1 hour. Then the mixture was cooled down at ambient temperature. The thus obtained formulation was a yellow clear and uniform liquid. The formulation contained 5 g/l of alpha-cypermethrin and had a density at 20° C. of 995 g/ml and a viscosity (Brookfield, 20° C., 100 s$^{-1}$) of 36 mPa·s. The pH of a 1% dilution (deionised water) was about 4.6. The dilution had a particle size of below 100 nm as determined by light scattering.

TABLE 1

| Ingredients (function) | Concentration ([g/l]; [% w/w]) |
| --- | --- |
| alpha-cypermethrin (active ingredient)[1] | 50 g/l; 5.03% w/w |
| (non-polar solvent)[2] | 200 g/l; 20.10% w/w |
| 2-heptanone (polar solvent) | 100 g/l; 10.05% w/w |
| anionic surfactant[3] | 132 g/l; 13.27% w/w |

TABLE 1-continued

| Ingredients (function) | Concentration ([g/l]; [% w/w]) |
|---|---|
| non-ionic surfactant (low HLB)[4] | 66 g/l; 6.63% w/w |
| non-ionic surfactant (high HLB)[5] | 22 g/l; 2.21% w/w |
| hexylene glycol (anti-freezing agent) | 200 g/l; 20.10% w/w |
| aq. citric acid (stabilizer) | 0.2 g/l; 0.02% w/w |
| biocide[6] | 2.0 g/l; 0.20% w/w |
| water | 995 g/l; 22.39% w/w |

[1] Cyano-(3-phenoxyphenyl)methyl-3-(2,2-dichlorethenyl)-2,2-dimethylcyclopropan-carboxylate
[2] solvesso ™ 200 ND (= mixture of aromatic hydrocarbon compounds)
[3] Tristyrylphenol ammonium sulfate ethoxylated with 16 ethylene oxide units
[4] $C_{13}$ fatty alcohol ethoxylated with 5 ethylene oxide units (HLB < 12)
[5] propylene oxide ethylene oxide block co-polymer (40% EO), HLB about 15,
[6] biocide containing 2-methyl-4-isothiazolin-3-one (2.5% w/w) and 1,2-benzisothiazolin-3-one (2.5% w/w)

The formulation of example 1 is chemically and physically stable upon storage at temperatures in the range of from −10 to 54° C. In particular neither chemical degradation nor phase separation upon storage at 50° C. for 5 weeks or upon storage for 12 weeks at 35° C. could be observed. No phase separation or crystallization occurred upon storage for 6 weeks at 0° C. or after 1 week at −10° C.

Furthermore, aqueous dilutions having a content of 0.1, 1 and 5% by weight of the formulation of example 1, based on the total weight of the resulting dilution, is stable towards separation and segregation of the active ingredient, e.g. no separation of material was observed visually or by optical means. An increase in particle size did not occur within 24 h. Filtration of a 0.5% dilution over a 150 μm sieve does not show any residue on sieve.

We claim:

1. An aqueous microemulsion formulation, comprising
a) at least one organic insecticide compound having a water solubility of not more than 5 g/l at 298 K and 1013 mbar;
b) at least one polar organic solvent selected from the group consisting of 2-heptanone and acetophenone;
c) at least one alcohol having from 6 to 8 carbon atoms;
d) at least one surfactant selected from anionic surfactants and non-ionic surfactants;
e) at least one non-polar organic solvent having a water solubility of not more than 1 g/l at 298 K and 1013 mbar; and
f) water,
wherein the at least one organic insecticide compound having a water solubility of not more than 5 g/l at 298 K and 1013 mbar is a pyrethroid compound P and wherein the average particle size in microemulsion upon dilution does not exceed 100 nm.

2. The formulation according to claim 1, wherein the at least one alcohol (c) is selected from the group consisting of 1-hexanol, 2-hexanol, 3-hexanol, 1-heptanol, 2-heptanol, 3-heptanol, 4-heptanol, 1-octanol, 2-octanol, 3-octanol, 4-octanol, 2-ethylhexanol, hexylene glycol, 2,5-hexanediol, cyclohexanol and benzyl alcohol.

3. The formulation according to claim 2, wherein the at least one alcohol (c) is hexylene glycol.

4. The formulation according to claim 1, wherein the at least one surfactant (d) is a surfactant mixture comprising
d.1) at least one anionic surfactant and
d.2) at least one non-ionic surfactant.

5. The formulation according to claim 1, wherein the anionic surfactant is selected from the group consisting of $C_1$-$C_{16}$-alkyl benzene sulfonates, $C_1$-$C_{16}$-alkyl naphthalene sulfonates, lignosulfonates, naphthalene sulfonate-formaldehyde condensates, $C_1$-$C_{16}$-alkyl naphthalene sulfonate-formaldehyde condensates, polyoxy-$C_2$-$C_3$-alkylene $C_8$-$C_{22}$-alkyl ether sulfates, polyoxy-$C_2$-$C_3$-alkylene $C_8$-$C_{22}$-alkyl ether phosphates, polyoxy-$C_2$-$C_3$-alkylene $C_1$-$C_{16}$-alkylbenzene ether sulfates, polyoxy-$C_2$-$C_3$-alkylene $C_1$-$C_{16}$-alkylbenzene ether phosphates, $C_8$-$C_{22}$-alkyl sulfates, $C_4$-$C_{18}$-dialkyl sulfosuccinates, polyoxy-$C_2$-$C_3$-alkylene mono-, di- or tristyryl phenyl ether sulfates, polyoxy-$C_2$-$C_3$-alkylene mono-, di- or tristyryl phenyl etherphosphates, polyoxyethylene polycarboxylates, polyphosphates, and mixtures thereof.

6. The formulation according to claim 1, wherein the non-ionic surfactant is selected from the group consisting of homo- or copolymers of $C_2$-$C_3$-alkylene oxides, polyoxy-$C_2$-$C_3$-alkylene $C_8$-$C_{22}$-alkyl ethers, polyoxy-$C_2$-$C_3$-alkylene $C_1$-$C_{16}$-alkylbenzene ethers, polyoxy-$C_2$-$C_3$-alkylene mono-, di- or tristyryl phenyl ethers, polyoxy-$C_2$-$C_3$-alkylene mono- or distyryl phenyl ether-formaldehyde condensates, and acetylene glycols.

7. The formulation according to claim 1, wherein the at least one surfactant (d) is a surfactant mixture comprising
d.1) at least one anionic surfactant;
d.2.a) at least one non-ionic surfactant having a hydrophilic-lipophilic-balance (HLB) of 12 or below; and
d.2.b) at least one non-ionic surfactant having a hydrophilic-lipophilic-balance (HLB) of above 12.

8. The formulation according to claim 7, wherein the at least one anionic surfactant (d.1) is selected from polyoxy-$C_2$-$C_3$-alkylene mono-, di- or tristyryl phenyl ether sulfates.

9. The formulation according to claim 7, wherein the at least one non-ionic surfactant (d.2.a) having a HLB of 12 or below is selected from polyoxy-$C_2$-$C_3$-alkylene $C_8$-$C_{22}$-alkyl ethers.

10. The formulation according to claim 7, wherein the at least one non-ionic surfactant (d.2.b) having a HLB of above 12 is selected from the group consisting of homo- or copolymers of $C_2$-$C_3$-alkylene oxides and polyoxy-$C_2$-$C_3$-alkylene mono-, di- or tristyryl phenyl ethers.

11. The formulation according to claim 1, wherein the at least one non-polar organic solvent (e) is selected from aromatic hydrocarbon compounds having 8 to 11 carbon atoms and mixtures thereof.

12. The formulation according to claim 1, wherein the at least one pyrethroid compound P is selected from the group consisting of acrinathrin, allethrin, barthrin, bifenthrin, bioallethrin, bioethanomethrin, biopermethrin, bioresmethrin, cismethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, esfenvalerate, fenfluthrin, fenpirithrin, fenpropathrin, fenvalerate, flucythrinate, fluvalinate, flurethrin, imiprothrin, metofluthrin, permethrin, phenothrin, prallethrin, profluthrin, pyresmethrin, pyrethrin I, pyrethrin II, resmethrin, tau-fluvalinate, tefluthrin, terallethrin, tetramethrin, tralomethrin, transfluthrin, etofenprox, flufenprox, halfenprox, protrifenbute and silafluofen.

13. The formulation according to claim 12, wherein the at least one pyrethroid compound P is selected from alpha-cypermethrin and flucythrinate.

14. The formulation according to claim 1, comprising
a) from 0.001 to 20% by weight of the at least one organic insecticide compound having a water solubility of not more than 5 g/l at 298 K and 1013 mbar;
b) from 0.1 to 40% by weight of the at least one polar organic solvent selected from 2-heptanone and acetophenone;

c) from 1 to 30% by weight of the at least one alcohol having from 6 to 8 carbon atoms;
d) from 1 to 40% by weight of the at least one surfactant selected from anionic surfactants and non-ionic surfactants;
e) from 1 to 40% by weight of the at least one non-polar organic solvent having a water solubility of not more than 1 g/l at 298 K and 1013 mbar; and
f) water ad 100% by weight
wherein the at least one organic insecticide compound having a water solubility of not more than 5 g/l at 298 K and 1013 mbar is a pyrethroid compound P.

15. A method of combating harmful organisms, which comprises contacting said harmful organisms, their habitat, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of the formulation as claimed in claim 1.

16. A method of combating harmful organisms, which comprises contacting said harmful organisms, their habitat, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of the formulation as claimed in claim 14.

17. A method for protecting crops from attack or infestation by harmful pests which comprises contacting a crop with an effective amount of the formulation as claimed in claim 1.

18. A method for protecting crops from attack or infestation by harmful pests which comprises contacting a crop with an effective amount of the formulation as claimed in claim 14.

19. A method for protecting seeds from attack or infestation by harmful pests which comprises contacting a seed with an effective amount of the formulation as claimed in claim 1.

20. The aqueous microemulsion formulation according to claim 1, wherein the average particle size is a Z-average particle diameter that can be determined by dynamic light scattering.

* * * * *